United States Patent [19]

Hirai

[11] 4,200,508

[45] Apr. 29, 1980

[54] METHOD AND COMPOSITION FOR DETECTING ANTIGENIC SUBSTANCES

[76] Inventor: Hidematsu Hirai, Kita 15-jo Nishi 7-chome, Kita-ku, Sapporo-shi, Hokkaido, Japan

[21] Appl. No.: 876,552

[22] Filed: Feb. 9, 1978

[30] Foreign Application Priority Data

Feb. 9, 1977 [JP] Japan .................................. 52/13183

[51] Int. Cl.² ..................... G01N 27/26; G01N 33/00; A61K 43/00
[52] U.S. Cl. ............................ 204/180 G; 204/299 R; 23/230 B; 424/12; 435/7
[58] Field of Search ........... 204/180 G, 180 S, 299 R; 210/500 M; 264/41; 23/230 B, 259; 424/12; 195/103.5 A

[56] References Cited

U.S. PATENT DOCUMENTS

| | | | |
|---|---|---|---|
| 3,773,625 | 11/1973 | Sternberger et al. | 195/103.5 A |
| 3,790,447 | 2/1974 | Hirata et al. | 195/103.5 A |
| 3,791,932 | 2/1974 | Schuurs et al. | 195/103.5 A |
| 3,839,153 | 10/1974 | Schuurs et al. | 195/103.5 A |
| 3,930,983 | 1/1975 | Sieber | 204/299 |
| 4,018,662 | 4/1977 | Ruhenstroth-Bauer et al. | 204/180 S X |
| 4,067,959 | 1/1978 | Bolz | 23/230 B |
| 4,071,315 | 1/1978 | Chateau | 23/230 B |

*Primary Examiner*—Arthur C. Prescott
*Attorney, Agent, or Firm*—Burgess, Ryan and Wayne

[57] ABSTRACT

A method and composition for detecting an antigenic substance by immunodiffusion using an antigenic substance to be detected labeled by a chromogenic enzyme. According to the method and the detection material of this invention, even a small amount of an antigenic substance can be easily detected.

28 Claims, No Drawings

METHOD AND COMPOSITION FOR DETECTING ANTIGENIC SUBSTANCES

BACKGROUND OF THE INVENTION

The present invention relates to a method of detecting an antigenic substance by immunodiffusion using as a reagent the antigenic substance to be detected labelled by a chromogenic enzyme and also to a detection material which is directly used for the detection of antigenic substance. More specifically, the present invention relates to a method of detecting antigenic substances which comprises addition of a test sample containing an antigenic substance to be detected and a material containing the antigenic substance to be detected labelled by a chromogenic enzyme to a supporting material uniformly containing therein the antibody or antiserum against the antigenic substance to be detected, an immunoreaction (or antigen-antibody reaction) to form an antigen-antibody complex, color reaction by the chromogenic enzyme in the complex, and the measurement of the degree of the diffusion of the enzyme in the complex.

Furthermore, the invention also relates to a material for detecting antigenic substances comprising a supporting material uniformly containing therein the antibody or antiserum of the antigenic substance to be detected and a material containing the antigenic substance to be detected labelled by a chromogenic enzyme.

The terms "antigenic substance" and "antigen" used in this invention mean not only a so-called complete antigen which possesses immunogenic reactivity but also haptens which do not possess immunogenicity but possess antigenic reactivity.

It therefore includes various antigens, for example serum protein antigens such as $\alpha$-fetoprotein, $\gamma$-globulin G, $\gamma$-globulin E, etc.; protein antigens such as an enzyme antigen, a toxin antigen, etc.; lipid antigens such as glycocalyx (cell wall polysaccharide), dextran and levan; other polysaccharide antigens comprising saccharides, a phospholipid, a lipopolysaccharide, a neutral lipid, etc; hapten antigens such as an azoprotein, a sulfurized substance, a 2,4-dinitrophenol protein, a steroid protein, a penicillin protein complex, a synthetic polypeptide, etc.; antinucleic acid antibody-producing nucleic acid antigens such as ribosomal, nuclear and phage antigens as well as, DNA, RNA, synthetic polynucleotides, a protein conjugate of a component constituting nucleic acid, etc; and blood group antigens such as an ABO antigen, a Lewis antigen, a forseman antigen, an MN antigen, a Rh antigen, etc.

The qualitative or quantitative detection of various antigenic substances is not only useful for the prophylaxis and diagnosis of various diseases and physiological abnormalities related to these substances but also widely utilized in some other research field for example, the determination of the molecular weight of proteins. For example, if the quantitative detection of a very small amount of human $\alpha$-fetoprotein is possible, it is useful for the diagnosis of hepatoma and the quantitative detection of a very small amount of human $\gamma$-globulin E or human gamma globulin E is likewise useful for the diagnosis of the diseases caused by immunological disorders.

Hitherto, as a method of detecting antigenic substances, for example, methods utilizing an antigen-antibody precipitation reaction or a hemagglutination or a complement fixation reaction are known. The method utilizing a hemagglutination or a complement fixation reaction is an indirect method and is such methods, the operation is complicated and the quantitative treatment thereof frequently encounters difficulty.

As the method utilizing the precipitation reaction, there is known an immunodiffusion method wherein the degree of the diffusion of the antigen-antibody complex formed by a precipitation reaction such as an antigen-antibody reaction, etc., is measured without separating the antigen-antibody complex and a method wherein the antigen-antibody complex formed by a precipitation reaction is separated by means of centrifugal precipitation, adsorption, gel filtration, etc., and thereafter the content of the unreacted antigen or the formed antigen-antibody complex is measured. The aforesaid immunodiffusion methods are classified according to the manner of diffusion, for example, into a single diffusion, a double radial diffusion and an immunoelectrophoresis (so-called rocket electrophoresis). Further, there is an immunodiffusion method employing staining and an immunodiffusion method using a radioisotope-labelled compound. These immunodiffusion methods are simple in operation but are usually inadequate for a quantitative measurement of a very small amount of an antigen for their limited detection sensitivity.

Furthermore, even in the immunodiffusion method employing an additional staining method, the quantitatively detectable range is at most about 10 $\mu$g./ml. Also, the immunodiffusion method using a radioisotope-labelled compound is disadvantageous in the operation process for its time consumption with obtaining the result and for the necessity of specific reagents and apparatus due to the radioactive substance. On the other hand, as the aforesaid latter method wherein the antigen-antibody complex formed is separated, there are known various methods such as a method using a radioisotope-labelled antigen (radioimmunoassay), a method using an enzyme-labelled antigen (enzyme immunoassay), etc. Among these methods, the radioimmunoassay has now been frequently used since the method can detect quantitatively a very small amount of an antigen. However, these methods are complicated in operation since it is inevitable in these methods to separate the antigen-antibody complex formed by a precipitation reaction from the unreacted antigen. Furthermore, since in the radioimmunoassay, it is necessary to use specific reagents and apparatus due to the use of radioactive substances, this method has the faults that the operation is complicated, it takes a long period of time to obtain the result and the cost is very high.

SUMMARY OF THE INVENTION

As the result of various investigations under such a technical level, the inventors have discovered that by employing an ordinary or electrophoresis-type immunodiffusion using an antigenic substance to be detected labelled by a chromogenic enzyme, a very small amount of an antigenic substance can be detected by a simple operation and the detection materials can be prepared easily and at a low cost. By the term "immunodiffusion" used in this invention is meant an immunoelectrophoresis utilizing electrophoresis and an ordinary immunodiffusion such as single diffusion, double radial diffusion, etc.

That is, when immunodiffusion is preformed by immunoelectrophoresis (so-called rocket electrophoresis) according to this invention, the immunodiffusion shows an excellent sensitivity comparable to that in radioimmunoassay and hence a very small amount of an antigenic substance can be quantitatively detected in a short period of time in a simpler manner. Also, when the immunodiffusion is performed by an ordinary immunodiffusion such as single diffusion and double radial diffusion according to another embodiment of this invention, the detection sensitivity is greatly increased and hence a very small amount of an antigenic substance can also be quantitatively detected in a simple manner. Moreover, the detection materials used for these methods can be prepared easily at a low cost.

For example, when Bovine Serum Albumin (BSA), a standard antigenic substance is used, the detection sensitivity for the antigen is at most about 10 μg./ml. according to conventional immunodiffusion methods but when the immunodiffusion is performed by the immunoelectrophoresis according to this invention, the antigen can be detected at a detection sensitivity of 125 ng. (nanograms)/ml. (80 times the detection sensitivity in conventional immunodiffusion methods) and when the immunodiffusion is performed by single radial diffusion according to another embodiment of this invention, the antigen can be quantitatively detected at a detection sensitivity of 500 ng./ml. (20 times that in conventional methods) as shown in Example 1 of this invention. Therefore, it is clear that the detection sensitivity for antigenic substances is greatly increased in this invention as compared with conventional methods. In particular, when immunoelectrophoresis is applied to the detection of α-fetoprotein according to this invention, the antigen can be quantitatively detected at a detection sensitivity of 10 ng./ml. (1000 times the detection sensitivity in conventional methods) as illustrated in Example 2 of this invention.

DETAILED DESCRIPTION OF THE PREFERRED EMBODIMENTS

The detection method of this invention will be described in detail together with the detection materials used in the method.

The detection method of this invention is the quantitative detection that a test material is added dropwise to holes on the detection material comprising the antibody or antiserum of an antigenic substance to be detected and a material containing an antigenic substance to be detected labelled by a chromogenic enzyme. For example, an antigen-containing standard solution having a given amount of an antigenic substance used as a standard test sample is applied for single radial immunodiffusion or an immunoelectrophoresis and then a color is developed by enzyme present in the immune complex.

The antibody used in this invention is not necessarily a purified antibody and if the specificity of antibody is sufficiently high, an unpurified antiserum may be employed without having any influence on the sensitivity of this invention, which is one of the excellent merits of this invention.

Gel-like carriers are preferably used as the support for the detection materials of this invention and examples of such gel-like carriers are gelatin, pectin, silica gel, starch, polysaccharides obtained from seaweeds such as agar, algin, carragheenin, etc., and synthetic polymers such as cross-linked polyacrylamide gel as described in U.S. Pat. No. 3,046,201 and the denatured celluloses as described in U.S. Pat. No. 3,360,440. Particularly preferred examples for the supporting material used in this invention are agar or agarose (purified agar which forms smooth and nonpolar gels preferably are used for gel electrophoresis), but the materials capable of being easily dispersed in water, having adequate rigidity so that the disc of the gel-like material can be tumbled without separation of the gel from the plate and capable of forming a transparent hydrogel can be preferably used in this invention.

The antigenic substance labelled by a chromogenic enzyme used in this invention is prepared by combining an antigenic substance to be detected with an enzyme which can catalyze the color reaction of a chromophor by subsequent treatment. The antigenic substance used in this case is the substance to be detected in the detection method of this invention and possesses the property capable of being combined with the enzyme used in this invention. The enzyme used in this case posesses the property of catalyzing the color reaction of a chromophor and capable of being combined with the aforesaid antigenic substance. Any antigenic substances and enzymes having the aforesaid properties can be used in this invention and in this case, it is preferred that they are purified before use. The purification of the antigenic substances and enzymes may be performed in the manner generally employed in the art. Furthermore, examples of the particularly preferred enzymes used in this invention are oxidation-reduction enzymes (or oxidoreductases) such as peroxidase, catalase, oxidase, various dehydrogenases, etc.

The combination reaction of the antigen and the enzyme is properly selected according to the kind of the antigen and the kind of the enzyme. It is preferred for maintaining the activity of the enzyme to protect the active site of the enzyme by a protective group in the combination reaction. In the case of using an oxidation-reduction enzyme such as peroxidase, the combination reaction is performed as follows; that is, after protecting the amino group at the active site of the enzyme using a protective group such as 1-fluoro-2,4-dinitrobenzene and then forming aldehyde at the saccharose moiety of the enzyme using an oxidative splitting agent at the site of the glycol moiety such as sodium periodate, the enzyme is combined with the antigen.

The purification of the enzyme-labelled antigen thus prepared is performed by the manner usually employed in the field of the art, such as extraction, dialysis, various chromatographies. The particularly preferred purification method is a column gel filtration of molecular sieve. It is necessary that the enzyme-labelled antigen keeps both the activity of enzyme and the activity of antigen and hence in the case of recovering the enzyme-labelled antigen at the purification thereof, the active fractions are collected confirming each activity.

The preparation of a purified antibody and/or purified antiserum can be performed in an ordinary manner.

The purified antibody, purified antiserum, or enzyme-labelled antigen thus prepared is then mixed with a suitable amount of the aforesaid supporting material such as agar and agarose and the mixture is spread over a flat plate. At mixing the aforesaid components, it is preferred to use a buffer solution possessing given pH and ionic strength.

A tris-hydrochloric acid buffer solution containing sodium chloride, amino acid buffer solution, phosphoric acid buffer solution, boric acid buffer solution, carbonic acid buffer solution, and barbituric acid buffer solution are exemplified for such buffer solution. A possible pH range is 5.0–9.5, and the pH is usually adjusted to 7.2–8.8. Furthermore, it is profitable to mix the aforesaid components at a temperature range of 40°–60° C. The amounts of the enzyme labelled antigen and the antibody may be properly selected according to the kind of the substance to be tested and of the supporting materials.

As the flat plate over which the aforesaid mixture is spread, a glass plate or a transparent plastic sheet having a size suitable for the detection is preferably used.

The detection material for immunoelectrophoresis is composed of the separate parts which uniformly contain the antibody and the enzyme-labelled antigen respectively, on a flat plate, as described above. Then, holes for the test samples are made in the former part containing the antibody. In this case, there is no restriction about the number of holes. On the other hand, the detection material for single radial diffusion is made on a flat plate by the supporting material which uniformly contains the antibody and holes for the test sample. There is also no restriction about the number of holes.

In the case of using the detection material for immunoelectrophoresis, a standard antigen or a test material is added into the holes for the test sample thus formed on the flat plate and immunoelectrophoresis is performed. In this case, the conditions of electric current, potential, migration time, etc., are properly selected and set considering the migration distance. The electrophoresis is performed using an electrophoresis buffer solution possessing given pH and ionic strength. In this case, as the electrophoresis buffer solution, buffer solutions usually used for electrophoresis, such as tris-hydrochloric acid buffer solution containing sodium chloride, aminoacid buffer solution, phosphoric acid buffer solution, boric acid buffer solution, carbonic acid buffer solution, and barbituric acid buffer solution are available. A pH range between 5–9 is useful but the buffer solution is usually adjusted to a pH of 7.2–8.8.

It is also preferred to perform the electrophoresis under cooling. By the application of the electrophoresis, the antigenic substance forms a precipitate (an antigen-antibody complex) with the antibody by an immune-reaction (antigen-antibody reaction) and the precipitate moves so long as the amount of the antigen present is in excess. The precipitates thus resulting are visualized as above and the peaks of these precipitates which are proportional to the concentration of the antigen are determined.

On the other hand, in the case of using the detecting material for single radial diffusion, the enzyme-labelled antigen and an antigen-containing standard solution or a test material are added into the holes of the detection material of this invention thus formed on a flat plate as described above to cause single radial diffusion. In this case, the conditions of diffusion time, etc., are properly selected considering the diffusion distance. The immunodiffusion is usually performed at room temperature. By the application of the single radial diffusion, the antigenic substance forms a precipitate (antigen-antibody complex) by an immuno-reaction with the antibody. The diameter of the precipitate's ring thus formed is proportional to the concentration of the antigen. Then, in each case, the precipitates are visualized by the enzyme conjugated to the antigen in combination with the chromophor coupled to the enzymes, respectively.

When the particularly preferred oxidation-reduction enzyme such as peroxidase, catalase, oxidase, various dehydrogenases, etc. is used azo compounds such as 3,3'-diaminobenzidine, etc., flavin, various cytochromes, etc., are used as the chromophor. Also, as the developing agent used in this invention, various oxidizing agents and reducing agents such as, for example, peroxides such as hydrogen peroxide, ozone, etc., oxygen, NADH (the nicotinamide adenine dinucleotic acid), FAD, thiol compounds, and metallic compounds such as iron, copper, etc., are available. By the combination of such materials, a particularly preferred color reaction can be applied.

In the case of employing a system using peroxidase, benzidine, and hydrogen peroxide, the reaction time is preferably from about 30 minutes to about 2 hours depending on the sharpness and facility of the color reaction. The reaction temperature is usually room temperature.

Then, the quantitative analysis of the test sample is performed by comparing the degree of the diffusion thus visualized as the antigen-antibody complex of a standard antigen of each concentration and the antibody that is, the height of the precipitates in immunoelectrophoresis or the diameter of the precipitate's rings in the case of immunodiffusion.

The detection method of this invention can also be applied to double diffusion, etc., as in the case of the above-described applications to immunoelectrophoresis and single radial diffusion although each diffusion method may be performed by each specific manner.

By conducting an immunoelectrophoresis test according to the present invention using a standard antigen or serum at known concentrations in a conventional manner, such as serial two-fold dilutions starting with a known concentration, a standard curve can be obtained by plotting the heights of the peaks against concentration. The concentration of antigen in the test sample can then be determined by conducting the immunodiffusion test with the test sample, measuring the peak, and referring to the standard curve.

EXAMPLE 1

Bovine Serum Albumin (BSA):

(a). Preparation of enzyme-labelled antigen:

To 1 ml. of a 0.5% peroxidase solution dissolved in a 0.3 M sodium hydrogencarbonate solution (pH 8.1) was added 0.1 ml. of a 1% 1-fluoro-2,4-dinitrobenzene solution dissolved in 100% ethanol and then the mixture was stirred at room temperature to block the amino group. After addition of 1.0 ml. of a 0.04–0.08 M sodium periodate solution, the mixture was stirred slowly at room temperature for about 30 minutes until the solution became yellow-green as the reaction proceeds with the saccharose moiety. Then, 1.0 ml. of a 0.16 M ethylene glycol solution was added to the solution and stirred for about one hour at room temperature. Thereafter dialysis was performed overnight at 4° C. against 0.01 M sodium carbonate buffer solution (pH 9.5) to eliminate excess sodium periodate.

To 3 ml. of the solution prepared above was added 1 ml. of a sodium carbonate buffer solution (pH 9.5) containing therein 0.1–0.5 mg. of purified Bovine Serum Albumin (BSA) and the mixture was stirred for 2–3 hours at room temperature.

Then, after further addition of 1–5 mg. of sodium borohydride to the above-prepared solution, the mixture was allowed to stand for longer than 3 hours at 4° C.

After stopping the reaction, the product was dialyzed against phosphate buffer containing sodium chloride (PBS) at 4° C., the resulting small amount of precipitates were removed by centrifugation.

Then, the supernatant solution was applied to a column of 85×1.5 cm. containing a molecular sieve such as Sephadex G100 or G200 washed previously with PBS. Gel filtration was performed at a flow rate of 10 ml./hr. Then, the fractions thus obtained were assayed for peroxidase activity and the BSA antigen activity and 25 ml. of the fractions showing both activities were collected to provide peroxidase-labelled Bovine Serum Albumin stock solution. By the method, more than 50% of the total peroxidase activity was recovered in the fractions.

(b). Preparation of the detection plate:

(i). Detection plate for immunoelectrophoresis:

Using separate agarose gels one containing 0.01% (w/v) anti-Bovine Serum Albumin (anti BSA) and the other containing about 5% (v/v) peroxidase-labelled BSA stock solution diluted by 0.05 M Veronal buffer (pH 8.6) at 46°–48° C., the antibody-containing part and peroxidase-labelled antigen-containing part were separately prepared at a thickness of about 2 mm. on a glass plate of 70 mm.×200 mm. Then, holes for the sample were formed in the antibody containing part in an ordinary manner.

(ii). Detection plate for single radial diffusion:

Using the agarose gel prepared for example by 0.01% (w/v) anti-Bovine Serum Albumin (anti BSA) to a 0.05 M Veronal (trademark of Barbital) buffer solution (pH 8.6) at 46°–48° C., the antibody-containing portion was prepared at a thickness of about 2 mm. on a glass plate of 150 mm.×150 mm. Then, holes were made at the antibody-containing portion in an ordinary manner.

(c). Detection of BSA:

(i). Immunoelectrophoresis:

To each hole formed in the detection material (the flat plate of the agarose gel) prepared in step (b)-(i) was added 10 μl. of a standard serum containing BSA adjusted to have different concentrations, for example, at serial two-fold dilutions (125–1,000 ng./ml.) or a test sample and the electrophoresis was performed at 2 mA/cm for 4 hours under cooling using electrophoresis buffer of a 0.05 M Veronal buffer solution (pH 8.6). Then, the detection material was immersed in a 0.05 M tris-hydrochloric acid buffer solution (pH 7.6) containing 0.025% (V/V) 3,3'-diaminobenzidine (DAB.4HCl, DOTITE) and 0.005% (V/V) hydrogen peroxide, whereby a migration diagram wherein the peroxidase active part was dyed brown was obtained. A standard curve was made by measuring the height of the peak thereof and the concentration of BSA was determined from this standard curve. In this example, even 125 ng./ml. of BSA could be detected.

(ii). Singe radial diffusion:

To each hole formed in the detection material (agarose flat plate) prepared in step (b)-(ii) were added the peroxidase-labelled BSA adjusted to have a concentration, for example, 5% (V/V) stock solution and a BSA standard prepared to have different concentrations (higher than 0.5 μg/ml., for example) at serial two-fold dilutions or test sample to perform the immunodiffusion for 48 hours. Then, the detection material was immersed in a 0.05 M tris-hydrochloric acid buffer solution (pH 7.6) containing 0.025% (V/V) 3,3'-diaminobenzidine (DAB.4HCl, DOTITE (trademark)) and 0.005% (V/V) hydrogen peroxide for one hour at room temperature, whereby a precipitate wherein the peroxidase active part was dyed in brown was obtained. A standard curve was made by measuring the diameter of the ring and the concentration of BSA was determined using the standard curve. In this experiment, even 500 ng./ml. of BSA could be detected.

EXAMPLE 2

Human α-fetoprotein:

(a). Preparation of enzyme-labelled antigen:

To 1 ml. of a 0.5% (W/V) solution of peroxidase dissolved in a 0.3 M sodium hydrogencarbonate solution (pH 8.1) was added 0.1 ml. solution of a 1% 1-fluoro-2,4-dinitrobenzene dissolved in 100% ethanol and then the mixture was stirred at room temperature to block the amino group. Thereafter, 1.0 ml. of a 0.04–0.08 M sodium periodate solution was added to the reaction mixture and the resultant mixture was stirred slowly for about 30 minutes at room temperature until the solution became yellow-green as the reaction proceeds with the saccharose moiety. Then, 1.0 ml. of a 0.16 M ethylene glycol solution was added. The mixture was stirred for about one hour at room temperature and dialysis was performed overnight at 4° C. against 0.01 M sodium carbonate buffer solution (pH 9.5) to eliminate excess sodium periodate.

To b 3 ml. of the above-prepared solution was added 1 ml. of a sodium carbonate buffer solution (pH 9.5) containing therein 0.1–0.5 mg. of human α-fetoprotein purified by Nishi's method (Biochem. Biophys. Acta.; 278, 293(1972)) and the mixture was stirred for 2–3 hours at room temperature to allow the reaction to proceed. Then, to the aforesaid solution was added 1–5 mg. of sodium borohydride and the mixture was allowed to stand for longer than 3 hours at 4° C. Then, the reaction was stopped, and the mixture was dialyzed against a phosphate buffer sodium chloride solution (PBS) at 4° C., and a small amount of precipitates formed were removed by centrifugation. Then, the supernatant solution was applied to a column of 85×1.5 cm. containing a molecular sieve such as Sephadex G100 or G200 washed beforehand with PBS, adjusting gel filtration rate to 10 ml./hour.

The peroxidase activity and the human α-fetoprotein antigenic activity of each fraction were assayed for their enzymatic activity and by the Ouchterlony method and approximately 25 ml. of the fractions showing both activities were collected to provide peroxidase-labelled human α-fetoprotein stock solution. By the method, more than 15% of the total peroxidase activity was recovered in the fractions.

(b). Preparation of the detection plate:

(i). The detection plate for immunoelectrophoresis:

Using the agarose gels containing 0.01% (V/V) anti-human α-fetoprotein or about 5% (V/V) of the peroxidase-labelled human α-fetoprotein-containing stock solution diluted by 0.05 M Veronal buffer solution (pH 8.6) at a temperature of 46°–48° C., the antibody-containing part and the peroxidase labelled antigen-containing part were separately prepared at a thickness of about 2 mm. on a glass plate of 70 mm.×200 mm. Thereafter, holes for the sample were made in the antibody-containing portion set on the glass plate in an ordinary manner.

(ii). Detection plate for single radial diffusion:

Using the agarose gel containing e.g., 0.01% (V/V) anti-human α-fetoprotein adjusted by 0.05 M Veronal buffer solution (pH 8.6) at 46°–48° C., the antibody-containing gel was set at a thickness of about 2 mm. on a glass plate of 150 mm.×150 mm. Then, holes were formed in the gel plate thus formed on the glass plate in a conventional manner.

(c). Detection of human α-fetoprotein:
(i). Immunoelectrophoresis:
To each hole of the detection material (the flat plate of the agarose gel) prepared in step (b)-(i) was added 10 μl. of a standard serum of human α-fetoprotein adjusted to have different concentrations (10–about 300 ng./ml.) or a test sample and the electrophoresis was performed at 2 mA/cm for 4 hours using a 0.05 M Veronal buffer solution (pH 8.6) as the electrophoresis buffer. Then, the detection material was immersed in a 0.05 M trishydrochloric acid buffer solution (pH 7.6) containing 0.0025% (V/V) 3,3'-diaminobenzidine (DAB.4HCl, DOTITE) and 0.005% (V/V) hydrogen peroxide for one hour at room temperature, whereby a migration diagram wherein the peroxidase active portion was dyed in brown was obtained. A standard curve was obtained by measuring the height of the peak and the concentration of α-fetoprotein was determined using the standard curve. By the experiment, 10 ng./ml. of human α-fetoprotein could be detected.

(ii). Single radial diffusion:
To each hole of the detection material (the flat plate of the agarose gel) prepared in step (b)-(ii) were added the peroxidase-labelled human α-fetoprotein and a standard serum of human α-fetoprotein adjusted to have different concentrations, for example, in serial two-fold dilutions (e.g., 78 ng./ml. to about 2.5 μg./ml.) or a test sample to perform immunodiffusion for 48 hours. Then, the detection material was immersed in a 0.05 M trishydrochloric acid buffer solution (pH 7.6) containing 0.025% (V/V) 3,3'-diaminobenzidine (DAB.4HCl), DOTITE) and 0.005% (V/V) hydrogen peroxide for one hour at room temperature, whereby a precipitate ring wherein the peroxidase active portion was dyed in brown was obtained. A standard curve was made by measuring the diameter of the brown precipitate ring and the concentration of human α-fetoprotein was determined using the standard curve. By the experiment, even 156 ng./ml. of human α-fetoprotein could be detected.

EXAMPLE 3

Human γ-globulin G (HGG):
(a). Preparation of enzyme-labelled antigen:
By following the manner as in Example 2 (a), peroxidase-labelled human γ-globulin G was prepared.
(b). Preparation of detection plate:
(i). Detection plate for immunoelectrophoresis:
Using the agarose gels containing 0.01% (V/V) anti-human γ-globulin G (anti-HGG) or about 5% (V/V) a peroxidase labelled HGG stock solution diluted by 0.05 M Veronal buffer solution (pH 8.6) at 46°–48° C., the antibody-containing part and the peroxidase-labelled antigen-containing part were separately set at a thickness of about 2 mm. on a glass plate of 70 mm.×200 mm. Then, holes for sample were formed at the antibody part formed on the glass plate by a conventional manner.
(ii). Detection plate for single radial diffusion:
Using the agarose gel containing, for example 0.01% (V/V) anti-HGG in 0.05 M Veronal buffer solution (pH 8.6) at 46°–48° C., the antibody-containing part was set at a thickness of about 2 mm. on a glass plate of 150 mm.×150 mm. Then, holes for sample were formed at the flat layer of the gel formed on the glass plate by a conventional manner.
(c). Detection of HGG:
(i). Immunoelectrophoresis:
To each hole of the detection material (flat plate or layer of the agarose gel) prepared in step (b)-(i) was added 10 μl. of a standard serum of HGG adjusted to have each different concentration (higher than 250 ng./ml.) or a test sample and electrophoresis was performed for 4 hours under cooling using a 0.05 M Veronal buffer solution (pH 8.6) as the electrophoresis. Thereafter, the procedure as in Example 2 (c)-(i) was followed. By the experiment, even 500 ng./ml. of HGG could be detected.
(ii). Single radial diffusion:
To each hole of the detection material (the flat plate of the agarose gel) prepared in step (b)-(ii) were added peroxidase-labelled HGG adjusted to 5% (V/V) stock solution and a standard serum of HGG adjusted to have each different concentration (higher than 100 ng./ml.) or a test sample proceeds the immunodiffusion for 48 hours. Thereafter, the procedure as in Example 2 (c)-(ii) was followed. By the experiment, even 300 ng./ml. of HGG could be detected.

EXAMPLE 4

Human γ-globulin E (Human IgE):
(a). Preparation of enzyme-labelled antigen:
By following the procedure as in Example 2 (a), peroxidase-labelled human γ-globulin E was obtained.
(b). Preparation of detection plate:
(i). Detection plate for immunoelectrophoresis:
Using the agarose gels each containing 0.01% (V/V) anti-human γ-globulin E (anti-human IgE) or about 5% (V/V) peroxidase-labelled human IgE stock solution diluted by 0.05 M Veronal buffer solution (pH 8.6) at 46°–48° C., the antibody-containing part and the peroxidase-labelled antigen-containing part were separately set at a thickness of about 2 mm. on a glass plate of 70 mm.×200 mm. Then, holes for samples were made in the antibody-containing portion formed on the glass plate by a conventional manner.
(ii). Detection plate for single radial diffusion:
Using the agarose gel containing 0.01% (V/V) anti-human IgE in 0.05 M Veronal buffer solution (pH 8.6) at 46°–48° C., the antibody-containing gel was set at a thickness of about 2 mm. on a glass plate of 150 mm×140 mm. Then, holes for sample were made in the plate of the agarose gel formed on the glass plate by a conventional manner.
(c). Detection of human IgE:
(i). Immunoelectrophoresis:
To each hole of the detection material (the flat plate of the agarose gel) formed in step (b)-(i) was added 10 μl. of the standard serum of human IgE adjusted to have different concentrations (higher than 250 ng/ml.) or a test sample and the electrophoresis was performed using a 0.05 M Veronal buffer solution (pH 8.6) for 4 hours under cooling. Then, the same procedure as in Example 2 (c)-(i) was followed. By the experiment, even 700 ng./ml. of human IgE could be detected.
(ii). Single radial diffusion:
To each hole of the detection material (the flat plate of the agarose gel) formed by step (b)-(ii) were added the peroxidase-labelled human IgE 5% (V/V) stock solution, and a standard serum of human IgE adjusted to have each different concentration (higher than 100 ng./ml.) or a test sample to perform the immunodiffusion for 48 hours. Then, the same procedure as in Example 2 (c)-(ii) was followed. By the experiment, even 350 ng./ml. of human IgE could be detected.
What is claimed is:

1. A method of detecting an antigen by immunodiffusion which comprises:
   (A) preparing a mixture of a support and an antibody against said antigen;
   (B) coating said mixture on a plate;
   (C) forming holes in said coating;
   (D) applying test sample to said holes in the presence of enzyme-labeled antigen;
   (E) conducting immunodiffusion to thereby obtain migration of the resulting antigen-antibody complex;
   (F) contacting said coated plate with a chromophore and a developing agent, whereby a measurable visible indication of the extent of migration is produced by the coupling of said enzyme and said chromphore; and
   (G) measuring the extent of migration of said complex.

2. The method of claim 1, wherein said immunodiffusion is immunoelectrophoresis, further comprising preparing a second mixture of a support and said enzyme-coupled antigen, coating said first-mentioned mixture on a portion of said plate, coating said second mixture on the remaining portion of said plate, and forming said holes in the coating containing said first mixture.

3. The method of claim 1, wherein said immunodiffusion is single radial diffusion and said enzyme-coupled antigen is applied to said holes with said test sample.

4. The method of claim 1, wherein the enzyme of said enzyme-labeled antigen is an oxidoreductase.

5. The method of claim 4, wherein said enzyme is peroxidase, catalase, oxidase, or a dehydrogenase.

6. The method of claim 1, wherein said support is agar, agarose, gelatin, pectin, silica gel, starch, algin, carrageenin, cross-linked polyacrylamide, or a denatured cellulose.

7. A structure for use in detecting an antigen by immunoelectrophoresis comprising a plate having coated on a portion thereof a uniform mixture of a support and an antibody against said antigen, and coated on the remaining portion thereof a uniform mixture of a support and an enzyme-labeled antigen.

8. The method of claim 1, wherein said enzyme-labeled antigen is prepared by coupling a blocking group to the amine group of the enzyme, oxidizing the saccharose moiety of said enzyme to form an aldehyde group, coupling said enzyme to the antigen, and removing said blocking group.

9. The method of claim 8, wherein said enzyme is an oxidoreductase.

10. The method of claim 9, wherein said enzyme is peroxidase, catalase, oxidase, or a dehydrogenase.

11. The method of claim 10, wherein the enzyme is peroxidase.

12. The method of claim 8, wherein the blocking agent supplying said blocking group is 1-fluoro-2,4-dinitrobenzene.

13. The method of claim 8, wherein said oxidizing is conducted using sodium periodate as the oxidizing agent.

14. The method of claim 1, wherein said chromophore is an azo compound.

15. The method of claim 14, wherein said chromophore is 3,3'-diaminobenzidine, flavin, or a cytochrome.

16. The method of claim 15, wherein said chromophore is 3,3'-diaminobenzidine.

17. The method of claim 1, wherein said developing agent is an oxidizing or reducing agent selected from the group consisting of peroxides, oxygen, NADH, FAD, thiols, and metal compounds.

18. The method of claim 17, wherein said metal compounds are compounds of iron or copper.

19. The method of claim 17, wherein said developing agent is hydrogen peroxide.

20. The method of claim 1, wherein said antigen is human α-fetoprotein, human γ-globulin G, or human γ-globulin E; said support is agar or agarose; said enzyme of said enzyme-labeled antigen is peroxidase; said chromophore is 3,3'-diaminobenzidine; said developing agent is hydrogen peroxide; and said immunodiffusion is immunoelectrophoresis or single radial diffusion.

21. The method of claim 1 wherein the antigen is human α-fetoprotein, human γ-globulin G, or human γ-globulin E.

22. The method of claim 5 wherein the chromogenic enzyme is peroxidase.

23. The method of claim 6 wherein the supporting material is agar or agarose.

24. The method of claim 1 wherein the antigenic is human γ-fetoprotein, human γ-globulin G, or human γ-globulin E; the support is agar or agarose; the enzyme is peroxidase; and the immunodiffusion is an immunoelectrophoresis or a single radial diffusion.

25. A structure for use in detecting an antigen by immunodiffusion comprising a uniform mixture of a support and an antibody or antiserum against said antigen and a uniform mixture of a support and said antigen labelled by a chromogenic enzyme.

26. The detection material of claim 25 wherein the antigen is human γ-fetoprotein, human γ-globulin G, or human γ-globulin E; the enzyme is peroxidase; and the support is agar or agarose.

27. The detection material of claim 7 wherein the antigen is human α-fetoprotein, human γ-globulin G, or human γ-globulin E; the enzyme is peroxidase; and the support is agar or agarose.

28. A method of detecting an antigen by immunodiffusion which comprises:
   (A) providing a test plate having a coating of a mixture comprising a support and an antibody against said antigen thereon, and holes formed in said coating;
   (B) applying test sample to said holes in the presence of enzyme-labeled antigen;
   (C) conducting immunodiffusion to thereby obtain migration of the resulting antigen-antibody complex;
   (D) contacting said coated plate with a chromophore and a developing agent, whereby a measurable visible indication of the extent of migration is produced by the coupling of said enzyme and said chromophore; and
   (E) measuring the extent of migration of said complex.

* * * * *